United States Patent
Bevacqua et al.

(10) Patent No.: US 6,171,605 B1
(45) Date of Patent: Jan. 9, 2001

(54) SELF TANNING COMPOSITIONS CONTAINING DHA AND PROPOLIS EXTRACT

(75) Inventors: Andrew J. Bevacqua, East Setauket, NY (US); Konstantinos M. Lahanas, Paramus, NJ (US); Neelam Muizzuddin, Bethpage; Nicolae Vrabie, Jackson Heights, both of NY (US)

(73) Assignee: Color Access, Inc., Melville, NY (US)

( * ) Notice: Under 35 U.S.C. 154(b), the term of this patent shall be extended for 0 days.

(21) Appl. No.: 09/349,913

(22) Filed: Jul. 8, 1999

(51) Int. Cl.[7] .................................................. A61K 7/00
(52) U.S. Cl. .................. 424/401; 424/59; 424/195.1; 514/532; 514/675; 514/844
(58) Field of Search .................. 424/401, 59, 195.1; 514/675, 844, 532

(56) References Cited

U.S. PATENT DOCUMENTS

| | | | |
|---|---|---|---|
| 2,949,403 | 8/1960 | Andreadis et al. | 167/90 |
| 4,708,865 | 11/1987 | Turner | 424/59 |
| 5,008,441 | 4/1991 | Nakanishi et al. | 560/75 |

*Primary Examiner*—S. Mark Clardy
*Assistant Examiner*—Michael A. Williamson
(74) *Attorney, Agent, or Firm*—Kenyon & Kenyon

(57) ABSTRACT

The present invention relates to self-tanning compositions comprising an effective amount of DHA in combination with an effective amount of propolis extract. The compositions provide self-tanning compositions which can produce a tan with enhanced coloration. The self-tan produced using the compositions of the present invention is more natural looking. In another embodiment of the present invention, the compositions comprise DHA combined with caffeic acid phenethyl ester.

18 Claims, 6 Drawing Sheets

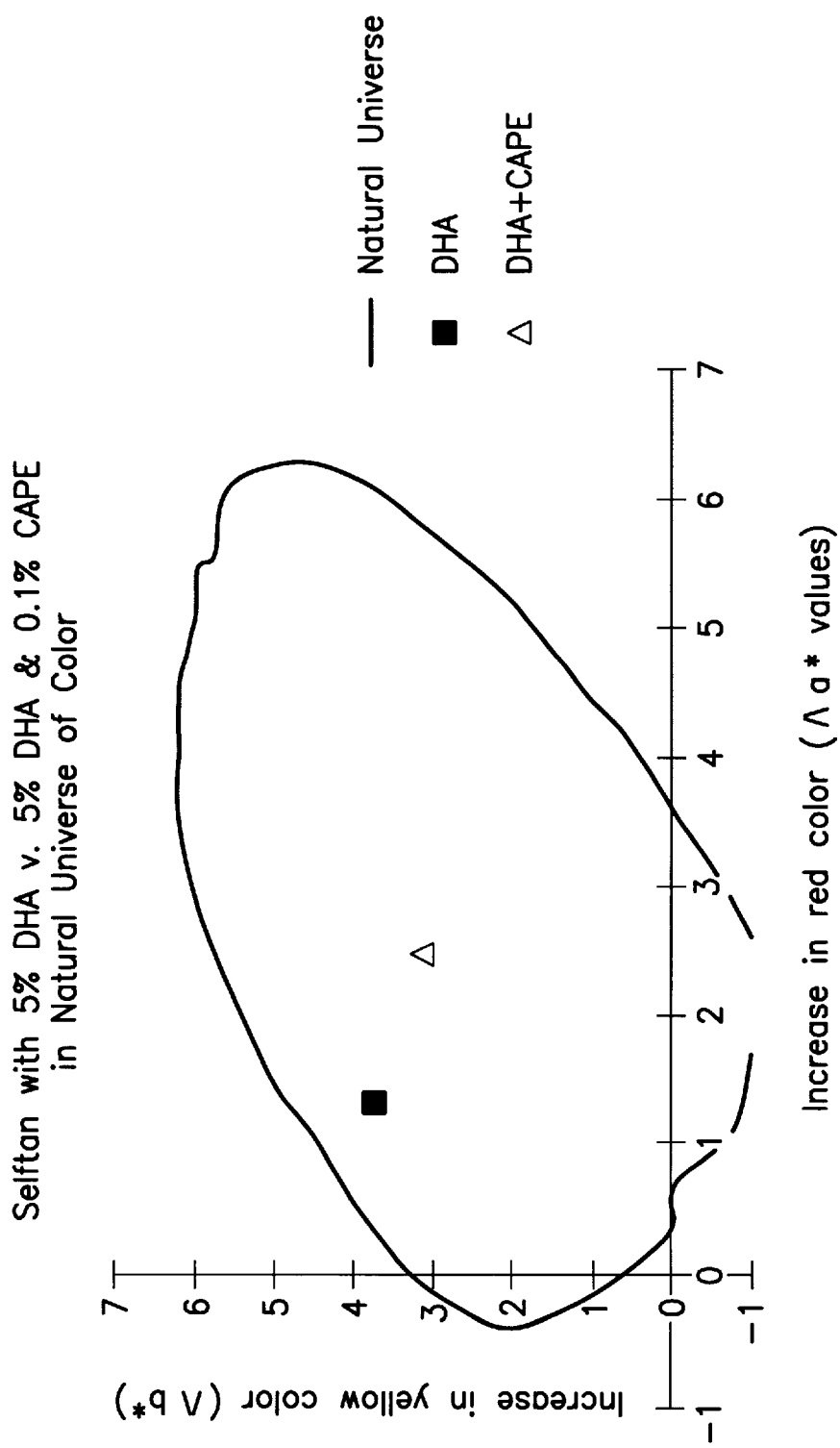

US 6,171,605 B1

SELF TANNING COMPOSITIONS CONTAINING DHA AND PROPOLIS EXTRACT

FIELD OF THE INVENTION

The invention relates to self-tanning compositions. More specifically, the invention relates to self-tanning compositions containing a combination of dihydroxyacetone with propolis which produce a more natural tan color when applied to the skin.

BACKGROUND OF THE INVENTION

A tanned complexion is still considered to be an attractive feature. And, a tan is still presently achieved primarily by exposing the skin to ultraviolet (hereinafter referred to as "UV") radiation. However, the concern about damage to the skin, particularly skin cancer, caused by exposing the skin to UV radiation from the sun or other sources such as, for example, sun lamps, has caused an increased interest in products that can produce a "self-tan" without the use of UV radiation. As a result, compositions useful for inducing a tan without exposure to the sun have been introduced for many years. For example, U.S. Pat. No. 2,949,403 discloses that the compound dihydroxyacetone (hereinafter referred to as "DHA") can be used for this purpose; since that report, DHA has been widely employed in commercial self-tanning products.

Many variations of the basic DHA formulation have been proposed to overcome or bolster some of the inherent inadequacies experienced when used alone as the active agent in a formulation. One of the most frequent problems encountered with DHA is the tendency to impart an orange cast to the skin of some users; this is caused by a preponderance of yellow color development relative to red color development. In an attempt to compensate for this undesirable result, various dyes have been incorporated with DHA (U.S. Pat. No. 4,708,865). However, the use of dyes in combination with DHA causes the color of the tan to look unnatural, and therefore remains unsatisfactory to the consumer as a self-tanning product.

As awareness regarding the damaging effects of prolonged exposure to the sun and UV radiation increases, the importance of self-tanning products grows commensurately. An important feature of a self-tanner is its ability to produce a very natural looking tan on the skin. A tan produced naturally by exposing the skin to the sun is a deep dark tan with a somewhat bronze coloration. Accordingly, a sunless self-tanning product is desired that can produce a tan comparable to the natural tan achieved by exposing the skin to the sun. Therefore, there remains a need for self-tanning compositions which meet these criteria. The present invention now satisfies these consumer needs.

SUMMARY OF THE INVENTION

The present invention relates to self-tanning compositions which comprise an effective amount of dihydroxyacetone (hereinafter referred to as "DHA") and an effective amount of propolis extract, or an active component thereof. The combination of DHA and propolis extract produces a self-tan that is darker and more natural looking than that produced by DHA alone. The coloration of the tan does not have the orange cast that a self-tan produced using DHA alone has. There is a shift to a greater content of red in the self tan which makes the self tan look more natural looking. In addition to the shift towards red, there is a lower content of yellow in the self tan. The self-tanning compositions of the present invention enhance the coloration of the self-tan because it has a natural look, similar to the natural tan produced by exposing the skin to the sun. Further, the present invention includes the combination of DHA with an effective amount of substantially pure caffeic acid phenethyl ester (hereinafter referred to as "CAPE"), one active component of propolis extract.

The invention also relates to a method of enhancing the self-tanning effect of DHA-containing compositions in which an effective amount of propolis extract, or active components thereof, is added to DHA-containing compositions. The present invention further includes the method of increasing the red content and lowering the yellow content of the self-tan by adding propolis extract, or active components thereof, such as CAPE, to DHA-containing compositions. Finally, the invention relates to a method for tanning the skin in the absence of the sun and comprises applying to the skin an effective amount of DHA and an effective amount of propolis extract.

BRIEF DESCRIPTION OF THE DRAWINGS

FIG. 6 compares the tonality, in terms of change in red and yellow color, of a self-tan produced by 5% DHA alone with a self-tan produced with a combination of 5% DHA and 0.1% CAPE.

DETAILED DESCRIPTION OF THE INVENTION

Figure 1:
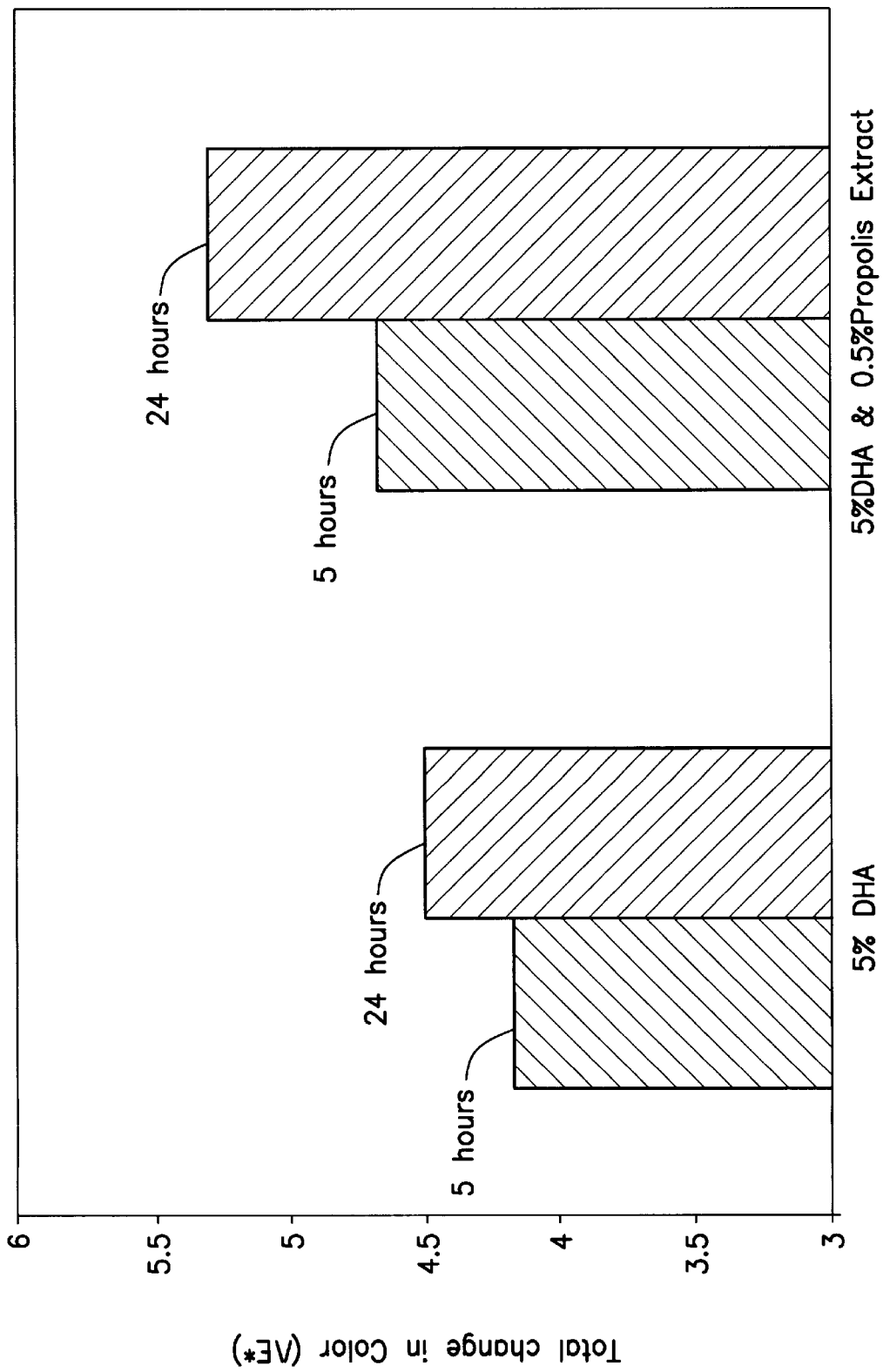
FIG. 1 illustrates the effect of 5% DHA compared with a combination of 5% DHA and 0.5% propolis extract as self-tanning agents.

Propolis, a naturally occurring material produced by honeybees, is composed of a variety of primary plant-derived pollens, waxes, oils, resins, polyphenols, and flavonoids. It is used by bees as a glue or cement in their hives. Hence, propolis is commonly referred to as "bee glue." With respect to humans, propolis has traditionally been reputed to have many therapeutic properties. For example, it has been stated that propolis is useful as an antimicrobial, an antioxidant, an anesthetic/analgesic, an anti-inflammatory, and for treatment of various skin conditions, such as acne and seborrhea. Propolis has not, however, previously been known to have any effect on self-tanning, nor has it previously been combined with DHA in a self-tanning composition.

It has now been surprisingly discovered that the presence of propolis extract with the known self-tanner DHA produces a natural looking tan having coloration similar to that of a tan created by UV radiation. The tan produced with an effective amount of propolis extract and an effective amount of DHA is also darker and richer than the tan produced using DHA by itself. The tan produced using DHA and propolis extract is more natural in appearance because it does not have an orange cast. By producing greater red coloration and less yellow coloration, the DHA and propolis tan is more natural looking than the tan with DHA alone.

The propolis extract employed in the present invention can be prepared using water, alcohol or hydroalcohol. The alcoholic extract of propolis can include alcohols such as, for example, isopropanol, ethanol, glycols, or other monohydric or polyhydric alcohols. The hydroalcoholic extract preferably uses a greater percent of alcohol than that of water. Preferably, the extract is in alcohol, more preferably ethanol. Propolis extract is prepared, for example, by macerating, for about 1 week, propolis in ethanol and filtering off impurities. The amount of propolis extract in the resulting solution can be from about 1 to about 85 percent; preferably the propolis extract is about 8 to about 12 percent solution of propolis extract in ethanol. Propolis is available commercially from Grant Industries, Elmwood Park, N.J. in a concentration of about 80% propolis extract in ethanol.

The propolis extract thus prepared is incorporated into a cosmetic formulation containing an effective amount of DHA. The amount of propolis extract solution is not critical, however, the propolis extract is present in an amount of about 0.05 to about 5.00 percent and DHA is present in an amount of about 1 to about 10 percent by weight of the composition. Assuming, for example, a 10 percent solution of propolis extract in ethanol, the propolis extract solution will be present in the amount of about 4 to about 6 percent of the weight of the composition such that the amount of propolis extract in the composition will be about 0.4 to about 0.6 percent. Preferably, propolis extract is present in an amount of about 0.4 to about 0.6 percent by weight of the composition and DHA is from about 4.0 to about 6.0 percent. Propolis extract in combination with DHA aids in reducing the yellow coloration and elevating the red coloration of the tan when combined with DHA such that a closer reproduction of a natural tan is achieved.

Color measurements are obtained using a Chromameter which measures the change in the value of difference in reflectance ($\Delta L^*$), difference in the increase in red coloration ($\Delta a^*$), and difference in the increase in yellow coloration ($\Delta b^*$). These delta values are measured against a baseline skin color value. These measurements are taken before treatment, and after 5 hours and 24 hours of treatment. After measuring $\Delta L^*$, $\Delta a^*$, and $\Delta b^*$, the total change in color ($\Delta E^*$) is calculated. The value of $\Delta E^*$ is calculated using the following equation.

$$\Delta E^* = [(\Delta L^*)^2 + (\Delta a^*)^2 + (\Delta b^*)^2]^{1/2}.$$

Chroma ($\Delta C^*$) is also calculated and plotted against reflectance, $\Delta L^*$, within the Natural Universe of Tan, which is a range of color of tan obtained by multiple or single exposures to the sun. Chroma, $\Delta C^*$, is calculated using the following equation.

$$\Delta C^* = [(\Delta a^*)^2 + (\Delta b^*)^2]^{1/2}.$$

Therefore, the term "effective amount" as used herein refers to any amount of propolis extract sufficient to alter the red coloration by a change in red color ($\Delta a^*$) of at least about 1.5, and sufficient to alter the yellow coloration of the tan by a change in yellow color ($\Delta b^*$) of at most about 2.5 when combined with an effective amount of DHA. Likewise, the term "effective amount" as used in connection with DHA refers to any sufficient amount of DHA such that when it is combined with propolis extract, will alter the red and yellow coloration of the tan as described. Further, as used herein, the term "propolis extract" includes all such extracts, and active components thereof.

The scope of the present invention encompasses not only propolis extract, per se, but also other active constituents of the propolis extract. More specifically, the active constituents responsible for the self-tanning properties of propolis extract in combination with DHA are extracted from solid propolis. There is at least one specific constituent of propolis, caffeic acid phenethyl ester (hereinafter referred to as "CAPE"), that that has been identified as contributing to certain advantageous self-tanning properties. Methods of preparing CAPE can be found in for example U.S. Pat. No. 5,008,441, incorporated herein by reference, or in organic synthesis references available to one of ordinary skill in the art. CAPE is also available commercially from, for example, MMP Inc., South Plainfield, N.J. CAPE has previously been known for its cytostatic properties, however, there has been no previous report of its ability to enhance the production of a self-tan.

Accordingly, the present invention also includes the surprising discovery that an effective amount of substantially pure CAPE and an effective amount of DHA enhance the coloration of the self-tan. As used herein, the term "substantially pure CAPE" refers to CAPE having a purity of at least about 75 percent, and preferably about 90 percent, as extracted from propolis using known methods known in the art. In addition, the term "effective amount" applies to CAPE as the term has been previously described with respect to propolis. In a preferred embodiment of the present invention, CAPE is present in an amount of about 0.01 to about 2.00 percent by weight of the composition. The amounts of DHA are as described above.

The present invention includes the method of enhancing the self-tanning effect of a DHA-containing composition by adding to the composition the effective amount of propolis extract. The compositions are prepared by routine methods of mixing which are known to the skilled artisan. The methods of the present invention are advantageous because they produce a natural colored tan using the combination of DHA with propolis extract, and comprise applying an effective amount of these compositions to the skin. The methods also include combining an effective amount of DHA and an effective amount of CAPE.

The self-tan, in terms of color and duration, is dependant upon the amount applied to the area to be self-tanned and the original color of the skin to be self-tanned. Larger quantities of the compositions in either a single application or multiple applications will affect the color of the skin surface and produce a deeper and darker self-tan. The compositions can be topically applied to any area of the skin intended for self-tanning such as, for example, the face, the legs and arms, and the torso. The self-tanning compositions are applied by rubbing them onto an area on the surface of the skin where the self-tan is desired. The self-tan is produced in about 1 to 5 hours and can be reapplied as necessary, or for example, about every 2 days. Therefore, the self-tanning compositions can be prepared in any form convenient for topical application to the skin. Such forms include, but are not limited to gels, creams, dispersions, emulsions (water-in-oil or oil-in-water), suspensions, solutions, lotions, foams, mousses, sprays and the like.

The self-tanning compositions may also be combined with photoaging-protective agents such as retinoids, i.e., Vitamin A and its derivatives, natural or synthetic. There are a number of such retinoids used for this purpose, including, but not limited to retinol (Vitamin A), retinoic acid (Vitamin A acid), retinal (Vitamin A aldehyde), and retinoic acid esters or amides, e.g., retinyl palmitate or retinyl acetate. In any such photo-aging composition, each active component is used in the amounts standard in the art for the treatment of extrinsic photo-aging symptoms.

In another embodiment of the present invention, the self-tanning compositions of the present invention may be combined with one or more sunscreens. The term "sunscreen" as used herein refers to any material which is capable of protecting human skin from ultraviolet radiation having a wavelength of from about 280 to about 400 nm, by effectively absorbing such radiation, and/or reflecting or scattering such radiation away from the surface of human skin. Examples of sunscreens with which the compositions of the present invention can be combined in this context are titanium dioxide, zinc oxide, benzophenones, p-amino benzoic acid (PABA), octyl dimethyl PABA, amyldimethyl PABA, octyl methoxycinnamate, 2-ethoxy p-methoxycinnamate, oxybenzone, homosalate, phenyl salicylate, glyceryl p-aminobenzoate, ethyl-p-glycosylimido benzoate and the like. In formulation, the sunscreen agent is used in the amounts normally used for that agent, and the DHA and propolis is used in the amounts stated above.

Various other optional ingredients may be included with the self-tanning compositions of the present invention, these include but are not limited to fragrances, perfumes, flavorings, preservatives, emollients, antiseptics, pigments, dyes, colorants, humectants, propellants, waterproofing agents, film formers, vitamins as well as other classes of materials whose presence may be cosmetically, pharmaceutically, medicinally or otherwise desirable. Common examples can be found in the CTFA International Cosmetic Ingredient Dictionary 4th Edition, The Cosmetic, Toiletry, and Fragrance Association, Inc., Washington, D.C., 1991, the contents of which are incorporated herein. The self-tanning compositions may also be useful in makeup products.

The compositions of the present invention may also comprise additional useful active ingredients which include, but are not limited to antioxidants, antimicrobials, analgesics, anesthetics, anti-acne agents, antidermatitis agents, antipruritic agents, anti-inflammatory agents, antihyperkeratolytic agents, anti-dry skin agents, antiperspirants, antipsoriatic agents, antiseborrheic agents, antiaging agents, antiwrinkle agents, skin lightening agents, depigmenting agents, wound-healing agents, corticosteroids, additional tanning agents, or hormones. The incorporation of the active in the formulation is determined by its solubility and/or stability therein.

The self-tanning compositions can be formulated with a variety of cosmetically and/or pharmaceutically acceptable carriers. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. Useful carriers include, for example, water, acetone, ethanol, ethylene glycol, propylene glycol, butane-1,3-diol, isopropyl myristate, isopropyl palmitate, or mineral oil. It will be apparent to the skilled artisan that the selected carrier must be compatible and relatively inert with respect to the self-tanning compositions. Methodology and components for formulation of compositions are well known, and can be found, for example, in Remington's Pharmaceutical Sciences, Eighteenth Edition, A. R. Gennaro, Ed., Mack Publishing Co., Easton Pa., 1990. Further, the carrier may be in any form appropriate to the mode of delivery, for example, solutions, colloidal dispersions, emulsions (oil-in-water or water-in-oil), suspensions, creams, lotions, gels, foams, mousses, sprays and the like. The selection of the mode of delivery for additional active ingredients, however, is limited to the mode of delivery chosen for the self-tanning compositions.

The invention is further illustrated by the following non-limiting example.

EXAMPLES

1. Preparation of a DHA/Propolis Self-Tanning Composition

| Ingredient | % Amount |
| --- | --- |
| Phase I | |
| Steareth-2 | 1.50 |
| Steareth-21 | 0.50 |
| Coco-Caprylate/Caprate | 4.00 |
| C12-15 Alcohols Benzoate | 5.00 |
| Laureth-1 | 2.00 |
| Glyceryl Stearate | 4.00 |
| Propylene Glycol | 3.00 |
| Phenyl Trimethicone | 5.00 |
| Octyl Palmitate | 4.00 |
| Octyl Hydroxystearate | 2.00 |
| 10% Propolis Extract in Ethanol | 5.00 |
| Phase II | |
| Purified Water | 15.50 |
| Glycerine | 3.00 |
| Butylene Glycol | 5.00 |
| Phase III | |
| Purified Water | 34.50 |
| DHA | 5.00 |
| Germall 115 | 1.00 |

Phase I ingredients and Phase II ingredients are combined in separate vessels and each combination is heated with stirring to 70° C. The combined Phase I ingredients are then added with stirring to the combined Phase II ingredients. The mixture is allowed to cool to 30° C. while stirring. The Phase III ingredients are combined and added to Phase I and II ingredients to form a final emulsion.

II. Self-Tanning Action of DHA and Propolis

Two formulas are prepared for testing as described in Example I: one formula contains 5.0% DHA (formula A), and the other contains 5.0% DHA and 5.0% of a 10% propolis extract solution (i.e., 0.5% propolis extract) (formula B). Each of seven panelists applies formula A to one arm and formula B to the other arm. The site of the arm was the volar forearm. Equal amounts of the product (800 μl) of the materials are dispensed, applied evenly and blended in until absorbed.

Figure 2:
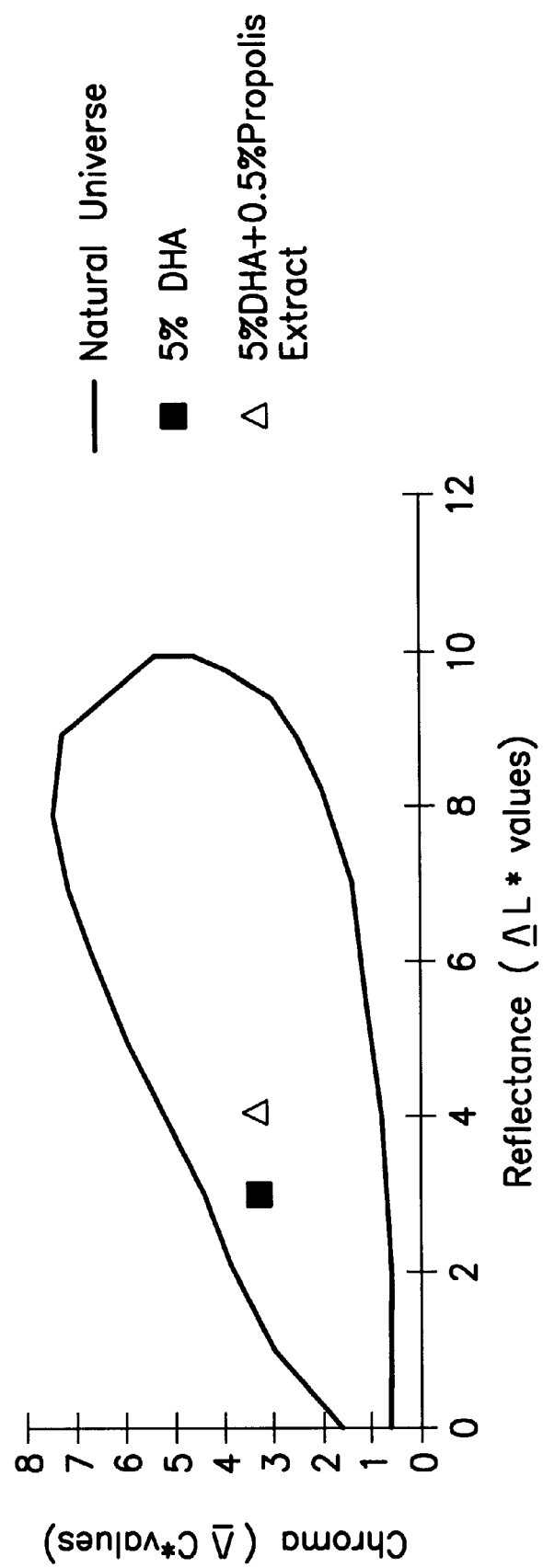
FIG. 2 illustrates the effect on tonality, in terms of reflectance, of a self-tan produced by 5% DHA compared with that of a combination of 5% DHA and 0.5% propolis extract within a natural universe of tan.
Figure 3:
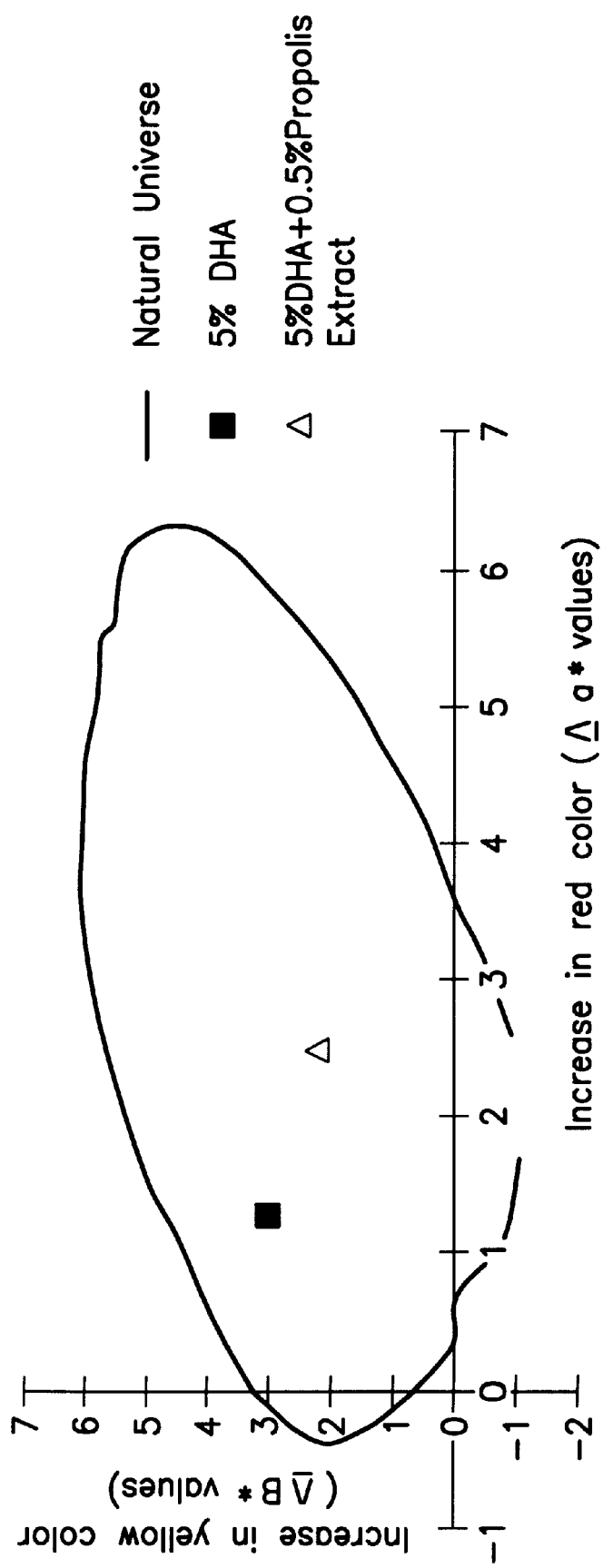
FIG. 3 illustrates the effect on tonality, in terms of change in red and yellow color, of a self-tan produced by 5% DHA compared with that of a combination of 5% DHA and 0.5% propolis extract.

Color measurements are obtained using a Chromameter as described above. Results are shown in FIGS. 1, 2 and 3. In FIG. 1, comparison of the self-tanning action of 5.0% DHA alone with that of the combination of 5.0% DHA with 0.5% propolis extract shows that the composition of the present invention produces a darker tan, as shown by the total change in color, $\Delta E^*$, than that produced by 5.0% DHA alone. In FIG. 2, comparison of the two formulas in terms of the difference in reflectance, ($\Delta L^*$), indicates that the combination of the present invention has a higher reflectance. And, in FIG. 3, a comparison of the two formulas with respect to the tonality of the self-tan produced by each shows that the composition of the present invention produces a greater difference in the increase in red color, Δa*, and a smaller difference in the increase in yellow color, Δb*, (i.e., a more natural-looking self-tan) than the self-tanning action of DHA alone does.

III. Preparation of a DHA/CAPE Self-Tanner

| Ingredient | % Amount |
|---|---|
| Phase I | |
| Dimethicone | 2.00 |
| Cyclomethicone | 21.34 |
| Cetyl dimethicone copolyol | 1.50 |
| Methyl glucose dioleate | 0.20 |
| Caprylic/Capric acid | 0.40 |
| Hydroxylated glycerides | 0.60 |
| BHT | 0.05 |
| Phase II | |
| Mavaceae extract | 0.40 |
| Bisabolol | 0.20 |
| Isoprene glycol | 3.00 |
| Phenoxyethanol | 0.40 |
| Nylon-12 | 0.60 |
| Phase III | |
| Purified water | 63.10 |
| Sodium chloride | 0.40 |
| Citric acid | 0.40 |
| Pantethine | 0.01 |
| Lactic acid | 1.30 |
| DHA | 5.00 |
| CAPE | 0.10 |
| Cyclodextrin | 1.00 |

Procedures are as described in Example I.

IV. Self-Tanning Action of DHA and CAPE

Two formulas are prepared for testing as described in Example III: one formula contains 5% DHA (formula A), and the other contains 5% DHA and 0.1% CAPE (formula B). Each of seven panelists applies formula A to one arm and formula B to the other arm. Equal amounts of the product (800 μl) of the materials are dispensed and blended in until absorbed.

Figure 4:
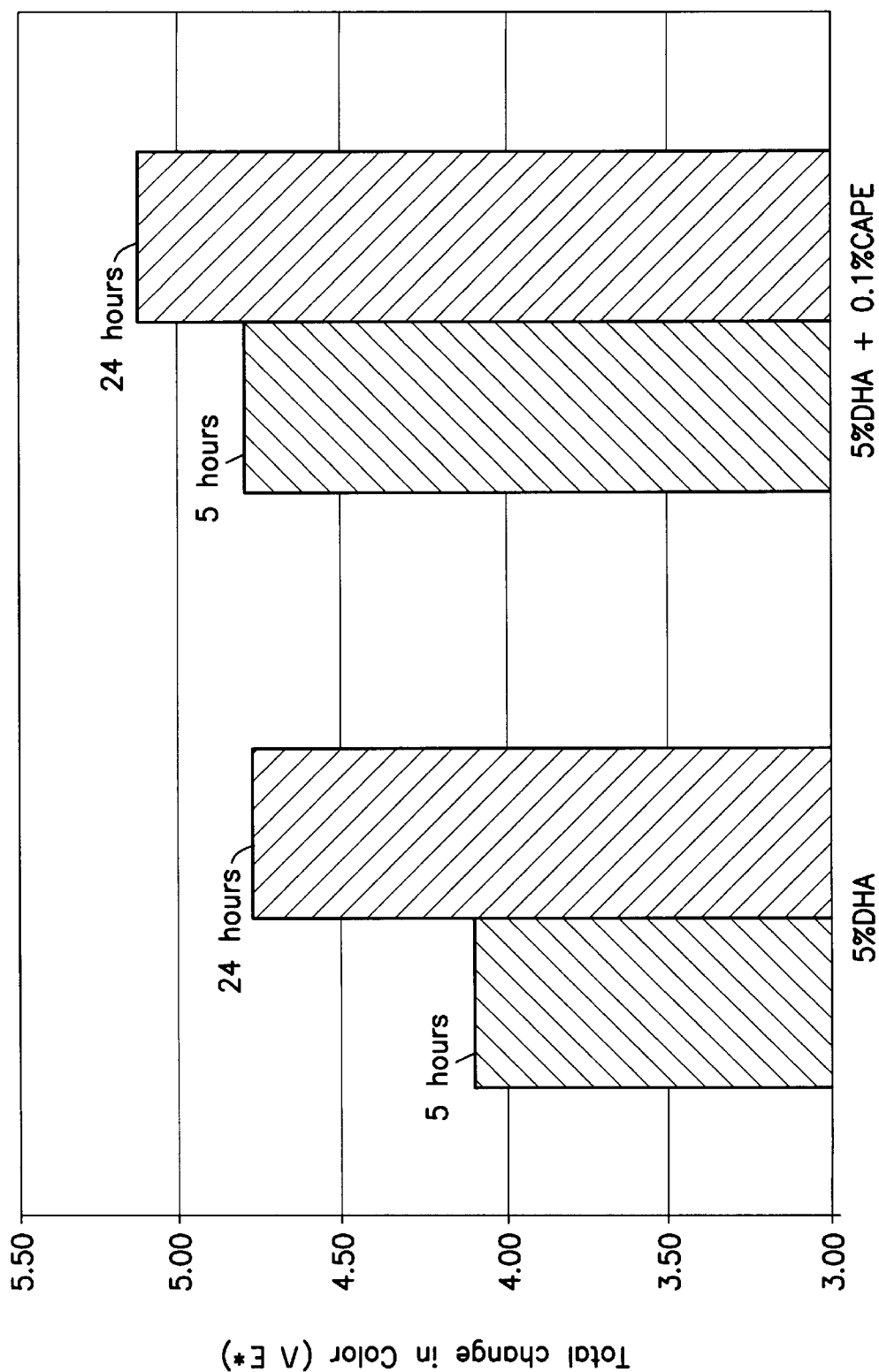
FIG. 4 compares the self-tanning action of 5% DHA alone with a combination of 5% DHA and 0.1% CAPE.
Figure 5:
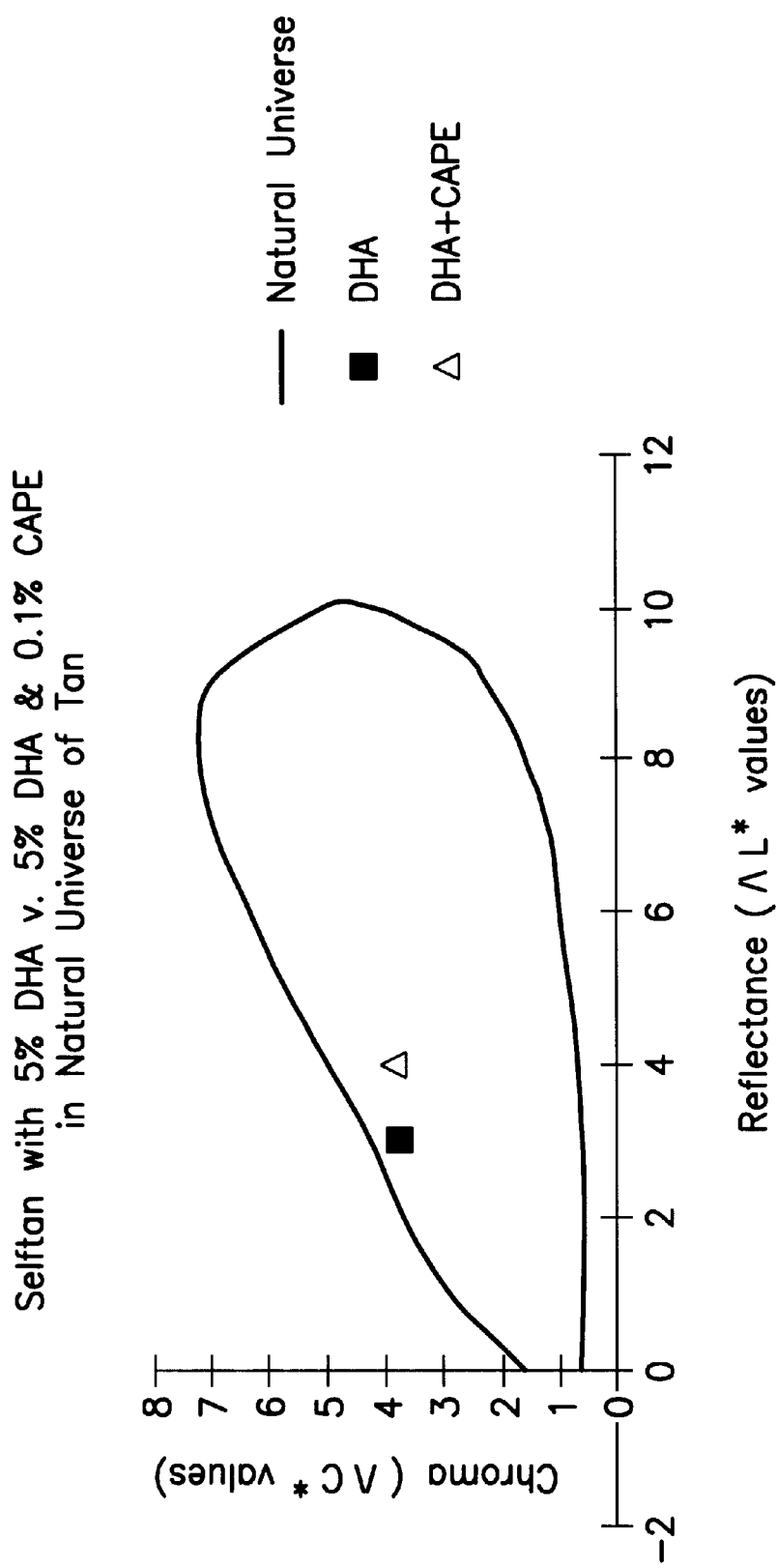
FIG. 5 compares the tonality, in terms of reflectance, of a self-tan produced by 5% DHA alone with a self-tan produced with a combination of 5 % DHA and 0.1 % CAPE.

Color measurements are obtained as described in Example II above and results are shown in FIGS. 4, 5 and 6. In FIG. 4, comparison of the self-tanning action of 5.0% DHA alone with that of the combination of 5.0% DHA with 0.1% CAPE shows that the composition of the present invention produces a much darker tan, as shown by the total change in color, ΔE*, than that produced by 5.0% DHA alone.

In FIG. 5, the difference in reflectance for 5.0% DHA alone and for 5.0% DHA in combination with 0.1% CAPE is illustrated. And in FIG. 6, comparison of the two formulas with respect to the tonality of the self-tan produced by each shows that the composition of the present invention produces a greater difference in the increase in red color, Δa*, and a smaller difference in the increase in yellow color, Δb*, (i.e., a more natural-looking self-tan) than the self-tanning action of DHA alone does.

What we claim is:

1. A self tanning composition comprising an effective amount of DHA and an effective amount of propolis extract.

2. The composition of claim 1 wherein said DHA is present in an amount of from about 1 to about 10 percent by weight.

3. The composition of claim 1 wherein said propolis extract is present in an amount of from about 0.05 to about 5.00 percent by weight.

4. The composition of claim 1 wherein said DHA is present in an amount of about 1 to about 10 percent by weight and said propolis extract is present in an amount of from about 0.05 to about 5.00 percent by weight.

5. The composition of claim 4 wherein said DHA is present in an amount of about 4.0 to about 6.0 percent, and propolis extract is present in an amount of from about 0.4 to about 0.6 percent by weight.

6. The composition of claim 1 wherein said propolis extract further comprises at least one active component.

7. The composition of claim 6 wherein at least one of said active components is caffeic acid phenethyl ester.

8. A self-tanning composition comprising an effective amount of DHA and an effective amount of substantially pure caffeic acid phenethyl ester.

9. The composition of claim 8 wherein said DHA is present in an amount of from about 1 to about 10 percent by weight.

10. The composition of claim 9 wherein said caffeic acid phenethyl ester is present in an amount from about 0.01 to about 2.00 percent by weight.

11. The composition of claim 10 wherein said DHA is present in an amount of about 1 to about 10 percent by weight and caffeic acid phenethyl ester is present in an amount of from about 0.01 to about 2.00 percent by weight.

12. A method of enhancing the self-tanning effect of a DHA-containing composition which comprises adding to the composition an effective amount of propolis extract.

13. The method of claim 12 wherein the composition comprises from about 1 to 10 percent weight of DHA.

14. The method of claim 13 wherein the composition comprises from about 1 to about 10 percent DHA, and from about 0.2 to about 10.0 percent propolis extract.

15. A method of artificially tanning the skin which comprises applying to the skin an effective amount of the composition of claim 1.

16. A method of artificially tanning the skin which comprises applying to the skin an effective amount of the composition of claim 8.

17. A method of increasing the red content and decreasing the yellow content of an artificial tan which comprises applying to the skin an effective amount of the composition of claim 1.

18. A method of increasing the red content and decreasing the yellow content of an artificial tan which comprises applying to the skin an effective amount of the composition of claim 8.

* * * * *